US012359247B2

(12) United States Patent
Bao et al.

(10) Patent No.: US 12,359,247 B2
(45) Date of Patent: Jul. 15, 2025

(54) METHODS OF PERFORMING GUIDE-SEQ ON PRIMARY HUMAN T CELLS (71) Applicant: ADOC SSF, LLC, South San Francisco, CA (US)

(72) Inventors: Xiaoyan Robert Bao, Foster City, CA (US); Kyle Jacoby, Burlingame, CA (US); William Lu, Oakland, CA (US)

(73) Assignee: ADOC SSF, LLC, South San Francisco, CA (US)

( * ) Notice: Subject to any disclaimer, the term of this patent is extended or adjusted under 35 U.S.C. 154(b) by 494 days.

(21) Appl. No.: 17/003,544

(22) Filed: Aug. 26, 2020

(65) Prior Publication Data
US 2021/0062248 A1 Mar. 4, 2021

Related U.S. Application Data (60) Provisional application No. 62/891,741, filed on Aug. 26, 2019.

(51) Int. Cl.
*C12Q 1/68* (2018.01)
*C12N 15/11* (2006.01)
*C12Q 1/6827* (2018.01)
*C12Q 1/6855* (2018.01)

(52) U.S. Cl.
CPC ............ *C12Q 1/6827* (2013.01); *C12N 15/11* (2013.01); *C12Q 1/6855* (2013.01); *C12N 2310/20* (2017.05); *C12N 2310/315* (2013.01)

(58) Field of Classification Search
CPC .... C12Q 1/6827; C12Q 1/6855; C12N 15/11; C12N 2310/20; C12N 2310/315
See application file for complete search history.

(56) References Cited

U.S. PATENT DOCUMENTS

| | | | |
|---|---|---|---|
| 5,912,148 | A | 6/1999 | Eggerding |
| 6,130,073 | A | 10/2000 | Eggerding |
| 6,210,891 | B1 | 4/2001 | Nyren et al. |
| 6,258,568 | B1 | 7/2001 | Nyren |
| 6,818,395 | B1 | 11/2004 | Quake et al. |
| 6,833,246 | B2 | 12/2004 | Balasubramanian |
| 6,911,345 | B2 | 6/2005 | Quake et al. |
| 6,969,488 | B2 | 11/2005 | Bridgham et al. |
| 7,115,400 | B1 | 10/2006 | Adessi et al. |
| 7,169,560 | B2 | 1/2007 | Lapidus et al. |
| 7,170,050 | B2 | 1/2007 | Turner et al. |
| 7,282,337 | B1 | 10/2007 | Harris |
| 7,302,146 | B2 | 11/2007 | Turner et al. |
| 7,313,308 | B2 | 12/2007 | Turner et al. |
| 7,329,492 | B2 | 2/2008 | Hardin et al. |
| 7,476,503 | B2 | 1/2009 | Turner et al. |
| 7,482,120 | B2 | 1/2009 | Buzby |
| 7,501,245 | B2 | 3/2009 | Quake et al. |
| 2013/0274147 | A1 | 10/2013 | Eshoo et al. |
| 2014/0038831 | A1 | 2/2014 | Suter et al. |
| 2014/0162897 | A1 | 6/2014 | Grunenwald et al. |
| 2016/0289637 | A1* | 10/2016 | Goldberg ................ A61P 19/10 |
| 2016/0304950 | A1* | 10/2016 | Joung ................... C12Q 1/6869 |
| 2017/0349914 | A1* | 12/2017 | Cox ........................ C12N 15/111 |
| 2018/0044700 | A1* | 2/2018 | Doudna .................. C12P 19/34 |

FOREIGN PATENT DOCUMENTS

| | | | |
|---|---|---|---|
| WO | WO 2012/065143 A1 | 5/2012 | |
| WO | WO 2015/200378 A1 | 12/2015 | |
| WO | WO 2017/193107 A2 | 11/2017 | |
| WO | WO 2018/013558 A1 | 1/2018 | |
| WO | WO 2019/089610 A1 | 5/2019 | |
| WO | WO 2019/195310 A1 | 10/2019 | |
| WO | WO 2020/167918 A1 | 8/2020 | |
| WO | WO 2020/205759 A1 | 10/2020 | |
| WO | WO 2022/015956 | * 1/2022 | ............. C12N 15/90 |

OTHER PUBLICATIONS

DeWitt et al. (2017) Genome editing via delivery of Cas9 ribonucleoprotein, Methods, 121-122, p. 9-15, doi:10.1016/j.ymeth.2017304.003 (Year: 2017).*
Seiki et al. (2018), Optimized RNP transfection for highly efficient CRISPR/Cas9-mediated gene knockout in primary T cells, Journal of Experimental Medicine, 215, p. 985-997 (Year: 2018).*
DeWitt et al. (2016), Selection-free genome editing of the sickle mutation in human adult hematopoietic stem/progenitor cells, Science Translational Medicine, vol. 8, issue 360ra134, p. 360ra134, doi:10.1126/scitranslmed.aaf9336 (Year: 2016).*
Rautela et al. (2018), Efficient genome editing of human natural killer cells by CRISPR RNP, bioRxiv preprint, doi: https://doi.org/10.1101/406934 (Year: 2018).*
Knipping et al. (2017), Genome-wide Specificity of Highly Efficient TALENs and CRISPR/Cas9 for T Cell Receptor Modification, Molecular Therapy Methods & Clinical Development, vol. 4, Mar. 2017, p. 213-236 (Year: 2017).*
Choi et al; Nature Methods, vol. 16, 2019, pp. 722-730.*
Adli et al., "The CRISPR tool kit for genome editing and beyond," Nat Communications 9:1911 (2018).
Boch et al., "TALEs of genome targeting," Nature Biotechnology 29(2):135-136 (2011).
Clark-Curtiss et al., "Analysis of Recombinant DNA Using *Escherichia coli* Minicells," Methods in Enzymology 101:347-362 (1983).
Cradick et al., "COSMID: A Web-based Tool for Identifying and Validating CRISPR/Cas Off-target Sites," Molecular Therapy—Nucleic Acids 3:e214 (2014).
DeWitt et al., "Genome editing via delivery of Cas9 ribonucleoprotein," Methods 121-122:9-15 (2017).
Gaj et al, "ZFN, TALEN, and CRISPR/Cas-based methods for genome engineering," Trends Biotechnol 31(7):397-405 (2013).

(Continued)

Primary Examiner — Jehanne S Sitton
(74) Attorney, Agent, or Firm — Baker Botts L.L.P.

(57) ABSTRACT

Disclosed herein are methods for identifying the effects, including off target effect, of genomic modification of primary cells. These methods are performed with high accuracy suitable for validating therapeutic T-cell engineering approaches.

17 Claims, 1 Drawing Sheet
Specification includes a Sequence Listing.

(56) References Cited

OTHER PUBLICATIONS

Gnirke et al, "Solution hybrid selection with ultra-long oligonucleotides for massively parallel targeted sequencing," Nature Biotechnology 27(2):182-189 (2009).
Kim et al., "DIG-seq: a genome-wide CRISPR off-target profiling method using chromatin DNA," Genome Research 28:1894-1900 (2018).
Lin et al., "CRISPR/Cas9 systems have off-target activity with insertions or deletions between target DNA and guide RNA sequences," Nucleic Acids Research 42(11):7473-7485 (2014).
Liu et al., "A fine-scale dissection of the DNA double-strand break repair machinery and its implications for breast cancer therapy," Nucleic Acids Res. 42(10):6106-6127 (2014).
MacLean et al., "Application of 'next-generation' sequencing technologies to microbial genetics," Nature Rev. Microbiol., 7:287-296 (2009).
Metzker, "Sequencing technologies—the next generation," Nat Rev Genet 11:31-46 (2010).
Morrison, "Transformation in *Escherichia coli*: Cryogenic Preservation of Competent Cells," J. Bacteriol. 132(1):349-351 (1977).
Stoddard, "Homing endonuclease structure and function," Q. Rev. Biophysics 38:49-95 (2006).
Tsai et al., "GUIDE-Seq enables genome-wide profiling of off-target cleavage by CRISPR-Cas nucleases," Nature Biotechnology 33(2):187-197 (2015).
Voelkerding et al., "Next-Generation Sequencing: From Basic Research to Diagnostics," Clinical Chem., 55:641-658 (2009).
International Search Report and Written Opinion mailed Jan. 19, 2021 in International Application No. PCT/US20/47964.
Zhang et al., "Efficient precise knockin with a double cut HDR donor after CRISPR/Cas9-mediated double-stranded DNA cleavage," Genome Biology 18(35):1-18 (2017).
Extended European Search Report dated Jun. 28, 2023 in Application No. EP 20857034.
Wienert et al., "Unbiased detection of CRISPR off-targets in vivo using DISCOVER-Seq," bioRxiv, Nov. 14, 2018 (Nov. 14, 2018), XP093056039, DOI: 10.1101/469635 Retrieved from the Internet: URL: https://www.biorxiv.org/content/10.1101/469635v1.full.pdf [retrieved on Jun. 20, 2023] 36 pages.
Gomes-Silva et al., "CD7-edited T cells expressing a CD7-specific CAR for the therapy of T-cell malignancies," Blood, 130(3):285-296 (2017).

\* cited by examiner

SEQUENCE LISTING

<160> NUMBER OF SEQ ID NOS: 11

<210> SEQ ID NO 1
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 5Phos-g
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (32)..(34)
<223> OTHER INFORMATION: Phosphorothioate linkage

<400> SEQUENCE: 1
gtttaattga gttgtcatat gttaataacg gtat                              34

<210> SEQ ID NO 2
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: 5Phos-a
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (32)..(34)
<223> OTHER INFORMATION: Phosphorothioate linkage

<400> SEQUENCE: 2
ataccgttat taacatatga caactcaatt aaac                              34

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
tcacgagcag ctggtttcta                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4
gggttttggt ggcaatggat                                              20

<210> SEQ ID NO 5
<211> LENGTH: 20
<212> TYPE: DNA
<213> ORGANISM: Artificial Sequence

```
<220> FEATURE:
<223> OTHER INFORMATION: Synthetic polynucleotide

<400> SEQUENCE: 5
caacagacac tgggatggtg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
gctctgttgg gctgagaatc                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
ctaactgggg gatggacaga                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
gagcttgagg tgctccattc                                              20

<210> SEQ ID NO 9
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(21)
<223> OTHER INFORMATION: n is a, c, g, or t

<400> SEQUENCE: 9
gagaatcaaa atcggtgaat ngg                                          23

<210> SEQ ID NO 10
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 10
gagaatcaaa atcggtgaat agg                                          23

<210> SEQ ID NO 11
<211> LENGTH: 23
<212> TYPE: DNA
<213> ORGANISM: Artificial Sequence
<220> FEATURE:
<223> OTHER INFORMATION: Synthetic polynucleotide
```

```
<400> SEQUENCE: 11
gagaatcaaa atcggtgaat agg                                              23
```

METHODS OF PERFORMING GUIDE-SEQ ON PRIMARY HUMAN T CELLS

CROSS-REFERENCE TO RELATED APPLICATIONS

This application claims priority to U.S. Provisional Application No. 62/891,741, filed on Aug. 26, 2019, the content of which is incorporated in its entirety, and to which priority is claimed.

SEQUENCE LISTING

The present specification refers to a Sequence Listing (submitted electronically as a .txt file named "0875200149.txt"). The .txt file was generated on Aug. 18, 2020, and is 2,937 bytes in size. The entire contents of the Sequence Listing are hereby incorporated by reference.

BACKGROUND OF THE INVENTION

Gene targeting is a method by which the genome can be directly edited, providing a path for engineering cell products, repairing mutations that cause genetic disorders, or creating mutations to study genes. Use of gene targeting in primary human T cells to create T cells with novel specificities enables clinically beneficial immunotherapies (e.g., TCR gene transfer and vaccines) that initiate, amplify, or attenuate immune responses to target antigens. Gene targeting relies on robust genome-editing reagents and methods for specific, targeted genome cleavage and sequence delivery. However, therapeutic use of gene targeting will require a detailed understanding of off-target effects of genome-editing reagents in a subject, such as cleavage and/or insertion activity at off-target genomic locations, to evaluate their safety prior to clinical use.

Existing methods to identify potential off-target insertion sites resulting from gene editing (e.g., by guide RNA-directed cleavage by Cas9) include computational simulations, such as CRISPR Off-target Sites with Mismatches, Insertions, and Deletions (COSMID) (Cradick et al., 2014), and a cell-based experimental method called Genome-wide, Unbiased Identification of Doublestranded breaks Enabled by Sequencing (GUIDE-Seq) (Tsai et al., 2015).

Computational simulations fail to identify off-target sites found by in vitro methods (see, e.g., Tsai et al., 2015) and thus do not have the reliability necessary to test therapeutic use of gene targeting reagents.

GUIDE-Seq shows promise in highly specific and sensitive identification of off-target genome editing in some specific cell lines that are permissive to double-stranded oligonucleotide (e.g., dsODN) transfection, such as U2OS or HEK293 cell lines. However, the approach provided in Tsai et al. cannot be used to identify off-target insertion sites in primary human cells. (see, e.g., Kim et al. (2018): "GUIDE-Seq, a widely used cell-based method, requires transfection of double-stranded oligonucleotides into cells. GUIDE-Seq cannot be used in certain cells that are refractory to transfection. Furthermore, double-stranded oligonucleotides are cytotoxic to many primary cells.") Further, the possibility of off-target cleavage sites arising from patient-specific genomic sequence variants cannot be addressed by experiments on cell lines.

What is needed, therefore, are highly sensitive, unbiased, and genome-wide methods to identify off-target cleavage/gene editing sites that are capable of being used in primary cells, e.g., primary human T cells, including patient-specific variants.

SUMMARY OF THE INVENTION

In certain embodiments, the present disclosure provides methods for detecting double-stranded breaks (DSBs) in genomic DNA of a primary cell, the method comprising: providing a nuclease composition capable of inducing a double-stranded break in the genomic DNA of a primary cell; providing a nucleotide composition comprising a blunt-ended double-stranded oligonucleotide (dsODN), wherein the dsODN is provided at an amount ranging from about 1 pmol to about 10 nmol; incubating the primary cell for a time sufficient for inducing DSBs in the genomic DNA of the cell, repairing the DSBs, and integrating a dsODN at one or more DSBs; amplifying a portion of the genomic DNA comprising the integrated dsODN; and sequencing the amplified portion of the genomic DNA, thereby detecting a DSB in the genomic DNA of the primary cell.

In certain embodiments, the dsODN is provided at an amount ranging from about 250 pmol to about 500 pmol. In certain embodiments, both strands of the dsODN are orthogonal to the genome of the cell. In certain embodiments, the 5' ends of the dsODN are phosphorylated. In certain embodiments, the dsODN comprises phosphorothioate linkages on both 3' ends. In certain embodiments, the dsODN comprises phosphorothioate linkages on both 3' ends and both 5' ends. In certain embodiments, the dsODN is between about 15 and about 50 nucleotides long.

In certain embodiments, amplifying a portion of the genomic DNA comprises fragmenting the genomic DNA; ligating ends of the fragmented genomic DNA with a universal adapter; performing a first round of polymerase chain reaction (PCR) on the ligated DNA with a first primer that is complementary to the integrated dsODN and a second primer that is complementary to the universal adapter; and performing a second round of PCR using a third primer that is a 3' nested primer and is complementary to the first primer, a fourth primer that is a 3' nested primer and is complementary to the second primer, and a fifth primer that is complementary to the fourth primer. In certain embodiments, the fifth primer a purification sequence, a binding sequence, an identification sequence, or a combination thereof.

In certain embodiments, the nuclease composition comprises a meganuclease, a zinc-finger nuclease, a TALEN nuclease, or a Cas nuclease. In certain embodiments, the nuclease composition comprises a ribonucleoprotein (RNP) complex. In certain embodiments, the RNP complex comprises a Cas9 nuclease and a guide RNA. In certain embodiments, the Cas9:guide RNA molar ratio is from about 1:4 to about 1:7. In certain embodiments, the Cas9:guide RNA molar ratio is about 1:6. In certain embodiments, the Cas9 nuclease is at an amount ranging from about 15 µg to about 30 µg per RNP complex. In certain embodiments, the Cas9 nuclease is at an amount of about 16 µg per RNP complex. In certain embodiments, the gRNA is at an amount ranging from about 500 pmol to about 750 pmol per RNP complex. In certain embodiments, the gRNA is at an amount of about 600 pmol per RNP complex.

In certain embodiments, the nuclease composition targets a TRAC locus. In certain embodiments, the nuclease composition targets a TRBC locus.

In certain embodiments, the guide RNA targets a TRAC locus and/or a TRBC locus. In certain embodiments, the DSB is an off-target DSB. In certain embodiments, the dsODN comprises a DNA barcode. In certain embodiments, the DNA barcode is randomized. In certain embodiments, the dsODN comprises a nucleotide sequence set forth in SEQ ID NO: 1 and SEQ ID NO: 2.

In certain embodiments, the nuclease composition is delivered by a non-viral delivery system. In certain embodiments, the nuclease composition is delivered by electroporation. In certain embodiments, the nucleotide composition is delivered by a non-viral delivery system. In certain embodiments, the nucleotide composition is delivered by electroporation.

In certain embodiments, the primary cell is a mammalian cell. In certain embodiments, the primary cell is a human cell. In certain embodiments, the human cell is a hematopoietic stem cell. In certain embodiments, the human cell is a T cell. In certain embodiments, the T cell is a cytotoxic T cell, a memory T cell, a regulatory T cell, a tumor-infiltrating T cell, a natural killer T cell. In certain embodiments, the T cell is a CD8+T cell or a CD4+T cell. In certain embodiments, the human cell is an NK cell. In certain embodiments, the primary cell is obtained from a subject. In certain embodiments, the subject is human.

BRIEF DESCRIPTION OF THE DRAWINGS

The foregoing and other objects, features, and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

DETAILED DESCRIPTION

The present disclosure relates to compositions and methods useful in connection with the detection of double-stranded breaks (DBS) in primary cells, e.g., T cells, undergone genetic editing.

Described herein are improved methods of identifying effects of genome editing in primary cells, including off-target effect. In certain embodiments, these methods provide highly accurate identification of such effect, e.g., off-target effects, by using a specifically designed double-stranded oligonucleotide that is inserted by the gene-editing mechanism, then subject to unbiased amplification for identification of effects, e.g., off-target effects. Due to the known challenges associated with genomic engineering and insertion of double-stranded oligonucleotides in primary cells, similar identification methods, including off-target identification methods, have yet to be achieved.

Nuclease-mediated gene editing of primary cells employing non-viral-mediated delivery has been previously described (see, e.g., PCT Publication WO2019/089610, "Primary Cell Gene Editing," incorporated herein in its entirety). As described in that publication, guide RNA-directed cutting by Cas9 has been successfully implemented to modify T cell receptor genes, which is useful to modify T cell specificity with several immunotherapeutic applications. However, guide RNA-directed cutting by Cas9 can occur at genomic sites that are not perfectly matched to the protospacer sequence, resulting in off-target cutting.

GUIDE-Seq is a cell-based method used to identify potential off-target sites by detecting the integration of a double-stranded oligodeoxynucleotide (dsODN) at sites of both on-target and off-target Cas9 cleavage (Tsai et al., 2015). However, GUIDE-Seq has been restricted to cell types permissive to dsODN transfection (Kim and Kim, 2018). In particular, GUIDE-Seq has not been performed using primary human T cells. Use of non-primary cell permissive cell lines to simulate off-target effects in primary human T cells also has shortcomings due to epigenetic differences between cell types or potential differences in ploidy. Further, the possibility of off-target cutting sites arising from patient-specific genomic sequence variants cannot be addressed by experiments on cell lines.

As described herein, according to certain embodiments, gene editing effects, including off target effects, in primary human T cells were successfully monitored by simultaneously electroporating the T cells with i) ribonucleoproteins (RNPs) complexed with TRAC or TRBC guide RNAs, and ii) a dsODN (in place of a patient-specific TCR plasmid), followed by unbiased amplification methods to identify specific off-target effects.

The details of various embodiments of the present disclosure are set forth in the description below. Other features, objects, and advantages of the present disclosure will be apparent from the description and the drawings, and the claims.

For purposes of clarity of disclosure and not by way of limitation, the detailed description is divided into the following subsections:
 1. Definitions;
 2. Guide-Seq;
 3. Gene Editing Systems;
 4. Compositions and Vectors;
 5. Kits; and
 6. Exemplary Embodiments.

1. Definitions

Unless defined otherwise, all technical and scientific terms used herein have the meaning commonly understood by a person skilled in the art. The following references provide one of skill with a general definition of many of the terms used in the presently disclosed subject matter: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

It is understood that aspects and embodiments of the invention described herein include "comprising," "consisting," and "consisting essentially of" aspects and embodiments. The terms "comprises" and "comprising" are intended to have the broad meaning ascribed to them in U.S. Patent Law and can mean "includes", "including" and the like.

As used herein, "antigen" includes any antigen including patient-specific neoantigens. An antigen includes any substance that can induce an immune response. The term "in vitro" refers to processes that occur in a living cell growing separate from a living organism, e.g., growing in tissue culture.

The term "in vivo" refers to processes that occur in a living organism.

"Host Cell" means cells into which exogenous nucleic acid has been introduced, including the progeny of such cells. Host cells include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "individual" or "donor" or "subject" is a mammal. In certain aspects, the individual or donor or subject is a human.

As used herein, a "polynucleotide" or a "nucleic acid" or a "nucleic acid are used interchangeably and includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Polynucleotide refers to any DNA (including but not limited to cDNA, ssDNA, and dsDNA) and any RNA (including but not limited to ssRNA, dsRNA, and mRNA) and further includes synthetic forms of DNA and RNA and mixed polymers comprising two or more of these molecules. One of skill in the art can understand which form is being referred to, e.g., based on the context in which the polynucleotide is being used. The polynucleotide may be linear or circular. In addition, the term polynucleotide includes both, sense and antisense strands, as well as single-stranded and double-stranded forms. The polynucleotide can contain naturally occurring or non-naturally occurring nucleotides. Examples of non-naturally occurring nucleotides include modified nucleotide bases with derivatized sugars or phosphate backbone linkages or chemically modified residues. Polynucleotides encompass DNA and RNA molecules which are suitable as a vector for direct expression of polypeptide of the invention in vitro and/or in vivo.

Unless specifically stated or otherwise apparent from context, as used herein the term "about" or "approximately" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Alternatively, the term can mean within an order of magnitude, preferably within 5-fold, and more preferably within 2-fold, of a value.

The term "substantially free of" is understood to mean less than a statistically significant amount of component (e.g., a contaminant or a viral component) present in a relevant total composition, including the component being at an undetectable level in the relevant total composition (i.e., "free of"). Less than a statistically significant amount can refer to a level of detection that does not qualify as having statistical confidence that a component is present in a relevant composition, such as a p-value greater than 0.1, 0.05, or 0.01. A composition can be substantially free of a component if the composition contains less than 10%, 9%, 8%, 7%, 6%, 5%, 4%, 3%, 2%, 1%, 0.5%, 0.1%, 0.05%, 0.01%, 0.001%, or 0.0001% of the component by mass/volume percentage concentration.

"Non-homologous end-joining" or "NHEJ" refers to ligation-mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

"Vector", "Expression Vector" and "Expression Construct" can be used interchangeably means the discrete elements that are used to introduce heterologous DNA into cells for either expression or replication thereof. As used herein, a vector can be engineered and used for in vivo or in vitro expression of a polypeptide gene product encoded by a coding sequence inserted into the vector.

As used herein, the term "barcode" refers to sequences of nucleotides, biomolecule components and/or subunits, or polymer component and/or subunits that are used for discriminating samples. In certain non-limiting embodiments, for example, a barcode can be a sequence of nucleotides in a polynucleotide.

A "kit" refers to any collection of two or more components that together constitute a functional unit that can be employed for a specific purpose. By way of illustration (and not limitation), one kit according to the present disclosure can include dsODN, other reagents, and consumables for performing the methods disclosed herein. The components of a kit can be packaged together, or they may be separately packaged. Kits according to this disclosure also optionally include instructions for use that describe the use of the kit, e.g., according to a method of this disclosure. The instructions can be physically packaged with the kit, or it can be made available to a user of the kit, for instance by interne access.

1.1 Other Interpretational Conventions

Ranges recited herein are understood to be shorthand for all the values within the range, inclusive of the recited endpoints. For example, a range of 1 to 50 is understood to include any number or fraction thereof, combination of numbers or fractions thereof, or sub-range from the group (including fractions of any of the numbers from the group) consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

2. Guide-Seq

The Genomewide Unbiased Identification of DSBs Evaluated by Sequencing (Guide-Seq) methods described herein provide highly sensitive, unbiased, and genome-wide methods for identifying the locations of engineered nuclease cleavage sites in primary human cells in which the non-homologous end-joining (NHEJ) repair pathway is active. In some embodiments, the method relies on the integration of short double-stranded oligodeoxynucleotides or oligonucleotides (dsODNs) into nuclease-induced breaks (a process presumed to be mediated by the NHEJ pathway) and then the use of the inserted dsODN sequence to identify the sites of genomic insertion. In some embodiments, an unbiased PCR-based deep sequencing approach in which the inserted dsODN sequence is used to selectively amplify the sites of genomic insertion for high-throughput sequencing, can be used. In some embodiments, genomic fragments including the inserted dsODNs can be selectively pulled down using an attached tag such as biotin, e.g., using solution hybrid capture.

Described herein is the development and validation of the GUIDE-Seq method in primary human cells.

The potential off-target sites identified by this initial sequencing process might also be analyzed for indel mutations characteristic of NHEJ repair in cells in which only the nuclease components are expressed. These experiments, which could be performed using amplification followed by deep sequencing, would provide additional confirmation and quantitation of the frequency of off-target mutations induced by each nuclease.

2.1. Double-Stranded Oligodeoxynucleotides and Double-Stranded Oligonucleotides (dsODNs)

In the methods described herein, a non-naturally occurring dsODN is delivered to or expressed in the primary human cells along with gene editing reagents. In some embodiments, both strands of the dsODN are orthologous to the genome of the cell (i.e., are not present in or complementary to a sequence present in, i.e., have no more than 10%, 20%, 30%>, 40%>, or 50%> identity to a sequence present in, the genome of the cell). The dsODNs can preferably be between about 15 and about 75 nucleotides long, e.g., about 15-about 50 nucleotides long, about 50-about 75 nucleotides long, about 30-about 35 nucleotides long, about 60-about 65 nucleotides long, or about 50-about 65 nucleotides long, or between about 15 and about 50 nucleotides long, e.g., about 20-about 40 nucleotides long, about 30-about 35 nucleotides long, e.g., about 32-about 34 nucleotides long. Each strand of the dsODN should include a unique PCR priming sequence (i.e., the dsODN includes two PCR primer binding sites, one on each strand) to facilitate unbiased amplification and identification. In some embodiments, the dsODN includes a restriction enzyme recognition site, preferably a site that is relatively uncommon in the genome of the cell, e.g., to validate insertion of the dsODN.

In some embodiments, the dsODNs are modified. In certain embodiments, the dsODNs comprise a chemical modification. In some embodiments, the 5' ends of the dsODN are phosphorylated. In certain embodiments, the 5' end of an dsODN is phosphorothiolate. In some embodiments, two phosphorothioate linkages are present on both 3' ends and both 5' ends. In some embodiments, the dsODN is blunt-ended. In some embodiments, the dsODNs include a random variety of 1, 2, 3, 4 or more nucleotide overhangs on the 5' or 3' ends.

The dsODN can also include one or more additional modifications, e.g., as known in the art or described in PCT Patent Publication No. WO2012/065143, "Polycomb-associated non-coding RNAs," incorporated herein by reference in its entirety. For example, in some embodiments, the dsODN is biotinylated. The biotinylated version of a dsODN tag can be used as a substrate for integration into the sites of genomic DSBs. The biotin can be anywhere internal to the dsODN (e.g., a modified thymidine residue (Biotin-dT) or using biotin azide), but not on the 5' or 3' ends. In some embodiments, such a biotin tag can be used to recover oligonucleotide fragments that contain the dsODN tag. Whereas in some embodiments, these sequences are retrieved and identified by nested PCR, in this approach they are physically pulled down by using the biotin, e.g., by binding to streptavidin-coated magnetic beads, or using solution hybrid capture; see, e.g., Gnirke et al, Nature Biotechnology 27, 182-189 (2009). The primary advantage is retrieval of both flanking sequences, which reduces the dependence on mapping sequences to a reference genome to identify off-target cleavage sites.

2.2. Amplification and Sequencing

The present disclosure provides methods comprising the amplification of the genomic DNA of a primary cell. In certain embodiments, without any limitation, the amplification of genomic DNA can be performed by polymerase-chain-reaction (PCR).

As used herein, "sequencing" includes any method of determining the sequence of a nucleic acid. Any method of sequencing can be used in the present methods, including chain terminator (Sanger) sequencing and dye terminator sequencing. In certain embodiments, Next Generation Sequencing (NGS), a high-throughput sequencing technology that performs thousands or millions of sequencing reactions in parallel, is used. Although the different NGS platforms use varying assay chemistries, they all generate sequence data from a large number of sequencing reactions run simultaneously on a large number of templates. Typically, the sequence data is collected using a scanner, and then assembled and analyzed bioinformatically. Thus, the sequencing reactions are performed, read, assembled, and analyzed in parallel; see, e.g., US 2014/0162897, as well as Voelkerding et al., Clinical Chem., 55: 641-658, 2009; and MacLean et al., Nature Rev. Microbiol., 7: 287-296 (2009).

Some NGS methods require template amplification and some that do not. Amplification-requiring methods include pyrosequencing (see, e.g., U.S. Pat. Nos. 6,210,89 and 6,258,568; commercialized by Roche); the Solexa/Illumina platform (see, e.g., U.S. Pat. Nos. 6,833,246, 7,1 15,400, and 6,969,488); and the Supported Oligonucleotide Ligation and Detection (SOLiD) platform (Applied Biosystems; see, e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,91 1,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476,503). See, e.g., US 2013/0274147; US2014/0038831; Metzker, Nat Rev Genet 11(1): 31-46 (2010).

Alternatively, hybridization-based sequence methods or other high-throughput methods can also be used, e.g., microarray analysis, NANOSTRING, ILLUMINA, or other sequencing platforms.

3. Gene Editing Systems

Off-target genome editing identification methods described herein are based on modifications to primary cells. In general, modified cells are modified such that they are genomically edited, or are capable of being genomically edited, using nuclease-mediated editing.

In some embodiments, nucleases promote editing through first directing cleavage at a specific nucleic acid sequence (i.e., a "defined nucleotide sequence" cleaved by a nuclease), e.g., a genome sequence, and subsequent editing results from non-templated based DNA repair, e.g., nuclease cleavage induced non-homologous end-joining DNA repair mechanisms, or results from template-based repair, e.g., homologous recombination DNA repair mechanisms.

A variety of nucleases that can be engineered to promote sequence-specific cleavage are known to those skilled in the art and include, but are not limited to, Clustered Regularly Interspaced Short Palindromic Repeats (CRISPR) family nuclease, a Transcription activator-like effector nuclease (TALEN) or derivative thereof, a zinc-finger nuclease (ZFN) or derivative thereof, and a homing endonuclease (HE) or derivative thereof. In particular, CRISPR-mediated gene editing systems can be used, such as the CRISPR/Cas9 editing system. Nuclease-mediated editing, and specifically CRISPR-mediated editing, is discussed in more detail in Adli M (The CRISPR tool kit for genome editing and beyond. Nat Commun. 2018 May 15;9(1): 1911), herein incorporated by reference for all that it teaches.

3.1. Cells and Cell Samples

The methods described herein can be used in any primary cell that is capable of repairing a DSB in genomic DNA. The two major DSB repair pathways in eukaryotic cells are Homologous recombination (HR) and Non-homologous end joining (NHEJ). Preferably, the methods are performed in primary cells capable of NHEJ. Methods for detecting NHEJ activity are known in the art; for a review of the NHEJ canonical and alternative pathways, see Liu et al, Nucleic Acids Res. Jun 1, 2014; 42(10):6106-6127.

In some embodiments, the methods described herein are used in primary human cells. In some embodiments, the primary human cells have been modified to add and/or remove genetic elements without the use of a viral delivery system. In some embodiments, the modified cell is substantially free of viral-mediated delivery components. In some embodiments, the primary human cell is a modified T-cell. In some embodiments, the modification comprises delivery of a polynucleotide comprising an exogenous nucleotide sequence, e.g., dsODN, to the primary cells.

In some embodiments, the methods described herein are performed on immune cells, such as T cells and B cells, from any appropriate patient-derived sample that comprises immune cells including, but not limited to, blood, plasma, peripheral blood mononuclear cell (PBMC) samples, bone marrow, tumor-infiltrating lymphocyte (TIL) samples, tissues, solid tumors, hematologic cancers, and liquid tumors, or any combination thereof. For example, both CD4+ and CD8+ T cells can be isolated from PBMCs or TILs using anti-CD4 and anti-CD8 fluorescent antibodies, with live populations of CD4+ and CD8+ single-positive cells sorted using fluorescence-activated cell sorting (FACS), to isolate only CD4+ or CD8+ cells for subsequent modification / off-target testing. In some embodiments, T cells that are positive for both CD4 and CD8 can be isolated using an anti-CD3 fluorescent antibody followed by FACS for subsequent modification / off-target testing. In some embodiments, CD4 and CD8 positive T cells can be isolated using a Prodigy machine (Miltenyi, Auburn Calif.). In some embodiments, CD4 and CD8 positive T cells can be isolated using a MACs column with CD4 and CD8 beads. In some embodiments, the sample is a blood sample. In some embodiments, the sample is a PBMC sample. In some embodiments, the sample is a solid tumor sample. In some embodiments, the sample is a hematologic tumor sample. In some embodiments, the sample is a bone marrow sample. In some embodiments, the sample is a tumor sample comprising tumor infiltrating lymphocytes. The T cells can be CD8+ T cells or CD4+ T cells. In some embodiments, the T cell is a CD8+ T cell. In some embodiments, the T cell is a CD4+ T cell. In some embodiments, the T cell is a human T cell. In some embodiments, the T cell is a human CD8+ T cell.

In certain embodiments, the methods disclosed herein are performed on primary cells. In certain embodiments, primary cells are cells are cells that are not cell lines engineered to be immortal. In certain embodiments, primary cells are isolated directly from living tissue (e.g., blood). In certain embodiments, primary cells can retain their original cellular and molecular features. In certain embodiments, primary cells can be used for the generation of genetically engineered cells. For example, without any limitation, primary cells are engineered to express a recombinant protein and used as cell therapy products. In certain embodiments, the primary cells are stem cells. In certain embodiments, the primary cells are pluripotent stem cells. In certain embodiments, the primary cells are hematopoietic stem cells. In certain embodiments, the primary cells are peripheral donor lymphocytes. In certain embodiments, the primary cells are T cells. In certain embodiments, the primary cells are NK cells.

3.2. Primary Cell Modification

The modified cells described herein can be modified using non-viral methods, e.g., the nuclease and CRISPR mediated gene editing systems described herein can be delivered to a cell using non-viral methods. While viral-mediated delivery (e.g., adenoviral, retroviral, and lentiviral based delivery methods) has been used to deliver nuclease and CRISPR mediated gene editing systems, viral-mediated systems can suffer from the viral systems also introducing components that lead to immunogenicity. For example, viral-mediated delivery components can include viral or virus-derived nucleotide sequences that are capable of integration into a genome. Thus, the modified cells described herein can be substantially free of viral mediated delivery components. The term "substantially free of viral-mediated delivery components" is understood to mean less than a statistically significant amount of one or more viral mediated delivery components present in a relevant total composition (e.g., a cell or populations of cells), including viral mediated delivery components being at an undetectable level in the relevant total composition (i.e., "the modified cells described herein can be free of viral-mediated delivery components"). Less than a statistically significant amount can refer to a level of detection that does not qualify as having statistical confidence that a viral mediated delivery component is present in a relevant composition, such asap-value greater than 0.1, 0.05, or 0.01. Viral-mediated delivery components can include viral proteins, such as viral structural proteins (e.g., capsid, envelope, and/or membrane-fusion proteins). In general, all peptides that are derived from integrated viral sequences or from introduced viral proteins can potentially be presented by MHC molecules on the cell surface, particularly MHC class I alleles, and can subsequently lead to immunogenicity.

In therapeutic contexts, such as adoptive cell therapies, immunogenicity can negatively impact therapeutic efficacy. Thus, non-viral delivery methods can be advantageous in modifying and editing cells to be used in adoptive cell therapies, such as adoptive T cell therapies. Therefore, in a particular aspect, MHC class I on the surface of a modified cell can be free of peptides derived from viral mediated delivery components or an integrated virus, wherein the integrated virus is operably associated with the viral mediated delivery components.

In some CRISPR systems, more than one CRISPR composition can be provided such that each separately target the same gene or general genomic locus at more than one defined nucleotide sequence. For example, two separate CRISPR compositions can be provided to direct cleavage at two different defined nucleotide sequences within a certain distance of each other, such as less than or equal to 10 base-pairs, less than or equal to 20 base-pairs, less than or equal to 30 base-pairs, less than or equal to 40 base-pairs, less than or equal to 50 base-pairs, less than or equal to 100 base-pairs, less than or equal to 200 base-pairs, less than or equal to 300 base-pairs, less than or equal to 400 base-pairs, less than or equal to 500 base-pairs, less than or equal to 1,000 base-pairs, less than or equal to 2,000 base-pairs, less than or equal to 5,000 base-pairs, or less than or equal to 10,000 base-pairs of each other. In some CRISPR systems, more than one CRISPR composition can be provided such that each separately target opposite strands of the same gene or general genomic locus. For example, two separate CRISPR "nickase" compositions can be provided to direct cleavage at the same gene or general genomic locus at opposite strands.

3.2. Nucleases and Ribonucleases

The present disclosure provides methods for assessing the cleavage profiles of nucleases and ribonucleases. Gene editing can be mediate by several different nucleases expressed in or otherwise delivered to the cell, including, without limitation, 1) meganucleases, 2) zinc finger nucleases (ZFN), 3) transcription activator effector-like nucleases (TALEN), and 4) Clustered Regularly Interspaced Short Palindromic Repeats (CRISPR) Cas RNA-guided nucleases (RGN). See, e.g., Gaj et al, Trends Biotechnol. 2013 Jul;31 (7):397-405. The nuclease can be transiently or stably expressed in the cell, using methods known in the art; typically, to obtain expression, a sequence encoding a protein is subcloned into an expression vector that contains a promoter to direct transcription. Suitable eukaryotic expression systems are well known in the art and described, e.g., in Sambrook et al, Molecular Cloning, A Laboratory Manual (4th ed. 2013); Kriegler, Gene Transfer and Expression: A Laboratory Manual (2006); and Current Protocols in Molecular Biology (Ausubel et al., eds., 2010). Transformation of eukaryotic and prokaryotic cells are performed according to standard techniques (see, e.g., the reference above and Morrison, 1977, J . Bacteriol. 132:349-351; Clark-Curtiss & Curtiss, Methods in Enzymology 101:347-362 (Wu et al, eds, 1983).

In certain embodiments, the nuclease is an endonuclease. In certain embodiments, the nuclease is a site-specific endonuclease (e.g., a restriction endonuclease, a meganuclease, a zinc finger nuclease, etc.).

In certain embodiments, the nuclease is a ZFN nuclease. The ZFN nuclease is generated by combining a zinc finger DNA-binding domain with a DNA-cleavage domain. A zinc finger domain can be engineered to target specific DNA sequences. This allows the zinc-finger nuclease to target desired sequences within genomes. The DNA-binding domains of individual ZFNs typically contain a plurality of individual zinc finger repeats and can each recognize a plurality of base pairs. A common method to generate a new zinc-finger domain is to combine smaller zinc-finger "modules" of known specificity. ZFN modulates the expression of proteins by producing double-stranded breaks (DSBs) in the target DNA sequence, which will, in the absence of a homologous template, be repaired by non-homologous end-joining (NHEJ). Such repair can result in deletion or insertion of base-pairs, producing frame-shift, and preventing the production of the harmful protein.

In certain embodiments, the nuclease is a TALEN nuclease. TALENs are restriction enzymes that can be engineered to cut specific sequences of DNA. TALEN systems operate on a similar principle as ZFNs. TALENs are generated by combining a transcription activator-like effector DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in the genome (Boch et al., *Nature Biotechnology;* 29(2):135-6 (2011)).

In certain embodiments, the nuclease is a meganuclease. Meganucleases recognize 15-40 base-pair cleavage sites. Meganucleases naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95).

In certain embodiments, the nuclease is a CRISPR associated protein. A CRISPR associated protein, e.g., a Cas9 protein, is used as genome-editing tool in the clustered regularly-interspaced short palindromic repeats (CRISPR) system. When complexed with an RNA molecule (e.g., guide RNA), the CRISPR associated protein targets a specific region of the host DNA to produce a single- or double-stranded break. gRNAs can be unimolecular (including a single RNA molecule, and referred to alternatively as chimeric) or modular (including more than one, and typically two, separate RNA molecules, such as a crRNA and a tracrRNA, which are usually associated with one another, for instance by duplexing). In certain embodiments, the CRISPR associated protein and the gRNA can be complexed into a ribonucleoprotein complex (RNP) for delivery to a cell, e.g., delivered by electroporation (see, e.g., DeWitt et al., Methods 121-122:9-15 (2017) for additional methods of delivering RNPs to a cell).

In some embodiments, a CRISPR-mediated gene editing system is used and off-target effects identified. A CRISPR-mediated gene editing system comprises a CRISPR-associated (Cas) nuclease and a RNA(s) that directs cleavage to a particular target sequence. An exemplary CRISPR-mediated gene editing system is the CRISPR/Cas9 systems comprised of a Cas9 nuclease and a RNA(s) that has a CRISPR RNA (crRNA) domain and a trans-activating CRISPR (tracrRNA) domain. The crRNA typically has two RNA domains: a guide RNA sequence (gRNA) that directs specificity through base-pair hybridization to a target sequence ("a defined nucleotide sequence"), e.g., a genomic sequence; and an RNA domain that hybridizes to a tracrRNA. A tracrRNA can interact with and thereby promote recruitment of a nuclease (e.g., Cas9) to a genomic locus. The crRNA and tracrRNA polynucleotides can be separate polynucleotides. The crRNA and tracrRNA polynucleotides can be a single polynucleotide, also referred to as a single guide RNA (sgRNA). While the Cas9 system is illustrated here, other CRISPR systems can be used, such as the Cpf1 system.

Nucleases can include derivatives thereof, such as Cas9 functional mutants, e.g., a Cas9 "nickase" mutant that in general mediates cleavage of only a single strand of a defined nucleotide sequence as opposed to a complete double-stranded break typically produced by Cas9 enzymes. In some embodiments, the guide RNA targets T-cell receptor genes, such as TRAC, TRBC1, or TRBC2.

In general, the components of a CRISPR system interact with each other to form a Ribonucleoprotein (RNP) complex to mediate sequence specific cleavage. In some CRISPR systems, each component can be separately produced and used to form the RNP complex. In some CRISPR systems, each component can be separately produced in vitro and contacted (i.e., "complexed") with each other in vitro to form the RNP complex. The in vitro produced RNP can then be introduced (i.e., "delivered") into a cell's cytosol and/or nucleus, e.g., a T cell's cytosol and/or nucleus.

3.2.1. RNP Complexes

In certain embodiments, the present disclosure comprises methods of delivering a ribonucleoprotein (RNP) complex into a primary cell. In certain embodiments, without any limitation, the RNP complex is obtained by combining a guide RNA (e.g., a sgRNA) with a Cas9 nuclease. An in vitro produced RNP complex can be complexed at different ratios of nuclease to gRNA. For example, an in vitro produced RNP complexes can be formed with sgRNAs complexed with Cas9 protein at a Cas9:sgRNA molar ratio of between 1:1-1:9, such as a Cas9:sgRNA molar ratio of 1:1, 1:2, 1:3, 1:4, 1:5, 1:6, 1:7, 1:8, or 1:9. An in vitro produced RNP complexes can be formed with sgRNAs complexed with Cas9 protein at a Cas9:sgRNA molar ratio of about 1:1, about 1:2, about 1:3, about 1:4, about 1:5, about 1:6, about 1:7, about 1:8, or about 1:9.

An in vitro produced RNP complex can be also be used at different amounts in a CRISPR-mediated editing system. For example, depending on the number of cells desired to be edited, the total RNP amount added can be adjusted, such as an increase in the amount of RNP complex added when editing a large number (e.g., $5 \times 10^7$) of cells in a reaction.

In some CRISPR systems, each component (e.g., Cas9 and an sgRNA) can be separately encoded by a polynucleotide and each polynucleotide introduced into a cell. In some CRISPR systems, each component can be encoded by a single polynucleotide (i.e., a multi-promoter or multicistronic vector, see description of exemplary multicistronic systems below) and introduced into a cell. Following expression of each polynucleotide encoded CRISPR component within a cell (e.g., translation of a nuclease and transcription of CRISPR RNAs), an RNP complex can form within the cell and can then direct site-specific cleavage. Some RNPs can be engineered to have moieties that promote delivery of the RNP into the nucleus. For example, a Cas9 nuclease can have a nuclear localization signal (NLS) domain such that if a Cas9 RNP complex is delivered into a cell's cytosol or following translation of Cas9 and subsequent RNP formation, the NLS can promote further trafficking of a Cas9 RNP into the nucleus.

In certain embodiments, the RNP complex comprises a Cas nuclease. In certain embodiments, the RNP complex comprises a gRNA. In certain embodiments, the RNP complex comprises two or more gRNAs. For example, without any limitation, the RNP complex comprises a Cas9 nuclease and a guide RNA targeting the TRAC locus and/or the TRBC locus.

3.2.2. Delivery of Ribonucleoprotein Complexes and dsODNs

Genetic modification of a cell (for example but not limited to a T cell) can be accomplished by using a nuclease capable of creating double-strand breaks into a genomic DNA and inserting a DNA construct into them. However, these processes can lead to the generation of off-target double-strand breaks which can impair the clinical use of the modified cell. Further, these processes are difficult to detect in primary cells because they are refractory to transfection and because of the nucleotides-related cytotoxicity.

The present disclosure provides methods comprising delivering nuclease compositions (e.g., ribonucleoprotein complexes) and nucleotide compositions (e.g., dsODNs) into primary cells.

Gene editing reagents or encoding polynucleotides, such as in vitro produced ribonucleoprotein (RNP) complexes, dsODN molecules, or vectors encoding these, may be inserted into the host cell via an appropriate method known, including, but not limited to, transfection, transduction, electroporation, lipofection, sonoporation, mechanical disruption, or viral vectors. Exemplary transfection reagents include, but are not limited to, FectorPro, Expifectamine, Lipofectamine, polyethyleneimine (PEI), Fugene, or any other transfection reagent that provides optimal transfection rates based on cell type, transfection system, transfection type, transfection conditions, and construct to be transfected. In some examples, Expifectamine is used to transfect mammalian cells. In some examples, polyethyleneimine is used to transfect mammalian cells. In some examples, FectorPro is used to transfect mammalian cells.

In a particular example, gene editing reagents can be delivered to a cell using a Nucleofector/Nucleofection® electroporation based delivery system (Lonza®). Other electroporation systems include, but are not limited to, MaxCyte electroporation systems, Miltenyi CliniMACS electroporation systems, Neon electroporation systems, and BTX electroporation systems. CRISPR nucleases, e.g., Cas9, can be produced in vitro (i.e., synthesized and purified) using a variety of protein production techniques known to those skilled in the art. CRISPR system RNAs, e.g., a sgRNA, can be produced in vitro (i.e., synthesized and purified) using a variety of RNA production techniques known to those skilled in the art, such as in vitro transcription or chemical synthesis.

Polynucleotides comprising genes encoding dsODN or RNP complex components may be transiently or stably expressed in the host cell. In some embodiments, such polynucleotide is integrated into the host genome. In other embodiments, the polynucleotide remains extra-chromosomal. Any appropriate genetic editing technique known in the art may also be employed to modify the host cell with the polynucleotide, including CRISPR/Cas9, zinc-finger nucleases, or TALEN nucleases.

In certain embodiments, the delivery of RNP complexes and/or dsODNs disclosed herein is performed by using viral delivery systems. In certain embodiments, the viral delivery system includes targeted and/or random integration. In certain embodiments, the viral delivery system can be Lentiflash° or other similar delivery system.

In certain embodiments, the delivery of RNP complexes and/or dsODNs disclosed herein is performed by using non-viral delivery systems. For example, a nucleic acid molecule can be introduced into a cell by administering the nucleic acid in the presence of lipofection, or by polylysine conjugation. Other non-viral means for gene transfer include transfection in vitro using calcium phosphate, DEAE dextran, electroporation, and protoplast fusion. Liposomes can also be potentially beneficial for the delivery of nucleic acids into a cell.

In certain embodiments, without any limitation, the delivery occurs via electroporation and comprises mixing the cells with the RNP complexes and/or dsODNs disclosed herein in a cuvette and applying one or more electrical impulses of defined duration and amplitude.

In certain embodiments, the RNP complexes and/or dsODNs are delivered by a combination of a vector and a non-vector based method.

In certain embodiments, the present disclosure comprises methods providing a ribonucleotide (RNP) complex. In certain embodiments, the RNP complex comprises a Cas9 nuclease. In certain embodiments, the Cas9 nuclease is present in an RNP complex in an amount of from about 0.5 µg to about 1000 µg, from about 5 µg to about 100 µg, from about 10 µg to about 100 µg, from about 25 µg to about 100 µg, from about 50 µg to about 100 µg, from about 75 µg to about 100 µg, from about 1 µg to about 75 µg, from about 1 μg to about 50 μg, from about 1 μg to about 25 μg, from about 1 μg to about 10 μg, from about 10 μg to about 20 μg, from about 15 μg to about 20 μg, from about .5 μg to about 10 μg, from about 0.5 μg to about 1 μg, from about 100 μg to about 200 μg, from about 200 μg to about 300 μg, from about 300 μg to about 400 μg, from about 400 μg to about 500 μg, from about 500 μg to about 600 μg, from about 600 μg to about 700 μg, from about 700 μg to about 800 μg, from about 800 μg to about 900 μg, or from about 900 μg to about 1000 μg and values in between.

In certain embodiments, the RNP complex comprises a guide RNA (gRNA). In certain embodiments, the gRNA is present in an RNP complex in an amount of from about 1 pmol to up to about 50,000 pmol, from about 1 pmol to about 100 pmol, from about 100 pmol to about 1000 pmol, from about 200 pmol to about 1000 pmol, from about 300 pmol to about 1000 pmol, from about 500 pmol to about 1000, from about 750 pmol to about 1000 pmol, from about 100 pmol to about 250 pmol, from about 100 pmol to about 500 pmol, from about 100 pmol to about 750 pmol, from about 250 pmol to about 500 pmol, from about 250 pmol to about 750 pmol, from about 250 pmol to about 1000 pmol, from about 500 pmol to about 750 pmol, from about 500 pmol to about 1000 pmol, from about 500 pmol to about 600 pmol, from about 500 pmol to about 650 pmol, from about 550 pmol to about 600 pmol, from about 550 pmol to about 650 pmol, or from about 1000 pmol to about 50,000 pmol, and values in between.

In certain embodiments, the present disclosure comprises methods providing a dsODN. In certain embodiments, the dsODN is provided at a concentration of about 200 pM to about 1000 pM, from about 300 pM to about 1000 pM, from about 400 pM to about 1000 pM, from about 500 pM to about 1000 pM, from about 600 pM to about 1000 pM, from about 800 pM to about 1000 pM, from about 200 pM to about 300 pM, from about 200 pM to about 400 pM, from about 200 pM to about 500 pM, from about 200 pM to about 600 pM, from about 200 pM to about 800 pM, from about 300 pM to about 500 pM, from about 300 pM to about 600 pM, from about 300 pM to about 800 pM, from about 300 pM to about 1000 pM, from about 400 pM to about 500 pM, from about 400 pM to about 600 pM, or from about 400 pM to about 800 pM, and values in between.

In certain embodiments, the dsODN is provided at an amount from about 1 pmol to about 10 nmol, from about 1 pmol to about 100 pmol, from about 100 pmol to about 200 pmol, from about 200 pmol to about 1000 pmol, from about 300 pmol to about 1000 pmol, from about 400 pmol to about 1000 pmol, from about 500 pmol to about 1000 pmol, from about 600 pmol to about 1000 pmol, from about 800 pmol to about 1000 pmol, from about 200 pmol to about 300 pmol, from about 200 pmol to about 400 pmol, from about 200 pmol to about 500 pmol, from about 200 pmol to about 600 pmol, from about 200 pmol to about 800 pmol, from about 300 pmol to about 500 pmol, from about 300 pmol to about 600 pmol, from about 300 pmol to about 800 pmol, from about 300 pmol to about 1000 pmol, from about 400 pmol to about 500 pmol, from about 400 pmol to about 600 pmol, from about 400 pmol to about 800 pmol, from about 1 nmol to about 2 nmol, from about 2 nmol to about 3 nmol, from about 3 nmol to about 5 nmol, or from about 5 nmol to about 10 nmol, and values in between.

In certain embodiments, the dsODN is provided at an amount of about 1 μg to about 100 μg, from about 5 μg to about 100 μg, from about 10 μg to about 100 μg, from about 20 μg to about 100 μg, from about 30 μg to about 100 μg, from about 50 μg to about 100 μg, from about 75 μg to about 100 μg, from about 1 μg to about 75 μg, from about 1 μg to about 50 μg, from about 1 μg to about 30 μg, from about 1 μg to about 20 μg, from about 1 μg to about 10 μg, from about 10 μg to about 20 μg, from about 15 μg to about 20 μg, or from about 15 μg to about 30 μg, and values in between.

In certain non-limiting embodiments, the present disclosure comprises methods providing a ribonucleotide (RNP) complex and dsODN to a primary cell in any of the quantities and concentration disclosed herein. For example, but without any limitation, the methods disclosed herein provide an RNP complex in a ratio of from about 1:5 to 1:7, wherein the RNP complex comprises a Cas9 nuclease in an amount of from about 10 μg to about 20 μg and a gRNA in an amount of from about 500 pmol to about 650 pmol; and the dsODN at a concentration of from about 400 pmol to about 500 pmol. In certain non-limiting embodiments, the methods disclosed herein provide an RNP complex in a ratio of from about 1:5 to 1:7, wherein the RNP complex comprises a Cas9 nuclease in an amount of from about 10 μg to about 20 μg and a gRNA in an amount of from about 500 pmol to about 650 pmol; and the dsODN at an amount of from about 15 μg to about 30 μg.

4. Compositions and Vectors

In certain embodiments, the present disclosure provides compositions used for performing the methods disclosed herein.

In certain embodiments, the present disclosure provides a "nucleotide composition." In certain embodiments, the nucleotide compositions comprise dsODN disclosed herein. In certain embodiments, the dsODN has a sequence comprising the nucleotide sequence set forth in SEQ ID NOs: 1-2. In certain embodiments, the nucleotide compositions comprise a polynucleotide encoding a nuclease. In certain embodiments, the nucleotide compositions comprise a polynucleotide encoding a Cas nuclease and a gRNA for the gene disruption of a genetic locus. In certain embodiments, the genetic locus is TRAC. In certain embodiments, the genetic locus is TRBC. Also provided are cells comprising such nucleotide compositions.

In certain embodiments, the present disclosure provides nuclease compositions. A "nuclease composition" comprises a nuclease protein or polynucleotide. In certain embodiments, the nuclease composition comprises a naturally occurring nuclease. In certain embodiments, the nuclease composition comprises a recombinant nuclease. In certain embodiments, the nuclease composition comprises an accessory molecule. For example, but without any limitation, the nuclease composition comprises a Cas9 nuclease and a gRNA targeting a genomic locus. Additional information on the nucleases encompassed by nuclease compositions are disclosed in Section 3.2 of the present disclosure.

The nuclease compositions and nucleotide compositions can be delivered into cells by methods described herein. Examples of the methods used for delivering nuclease compositions and/or nucleotide composition are described in Section 3.2.2 of the present disclosure.

5. Kits

The presently disclosed subject matter provides kits for performing the methods disclosed herein. In certain embodiments, the kit comprises dsODN. In certain embodiments, the kit comprises a nuclease. In certain embodiments, the kit comprises a nuclease composition. In certain embodiments, the kit comprises the nucleic acids disclosed herein. In certain embodiments, the kit comprises nucleotide compositions. In certain embodiments, the kit comprises adapters;

reagents and/or enzymes for end repair and/or ligation; exonucleases; endonucleases; and/or instructions for use in a method described herein.

If desired, the kits are provided together with instructions for performing the methods disclosed herein. In certain embodiments, the instructions include at least one of the following: description of the dsODN; manual of use; technical protocols; and/or references. The instructions may be printed as a separate sheet, or available via electronic means.

6. Exemplary Embodiments

A. In certain non-limiting embodiments, the present disclosure provides a method for detecting double-stranded breaks (DSBs) in genomic DNA of a primary cell, the method comprising providing a nuclease composition capable of inducing a double-stranded break in the genomic DNA of a primary cell; providing a nucleotide composition comprising a blunt-ended double-stranded oligonucleotide (dsODN), wherein the dsODN is provided at an amount ranging from about 250 pmol to about 500 pmol; incubating the primary cell for a time sufficient for inducing DSBs in the genomic DNA of the cell, repairing the DSBs, and integrating a dsODN at one or more DSBs; amplifying a portion of the genomic DNA comprising the integrated dsODN; and sequencing the amplified portion of the genomic DNA, thereby detecting a DSB in the genomic DNA of the primary cell.

A1. The foregoing method of A, wherein the dsODN is provided at an amount ranging from 250 pmol to about 500 pmol.

A2. The foregoing method of A or A1, wherein both strands of the dsODN are orthogonal to the genome of the cell.

A3. The foregoing method of A-A2, wherein the 5' ends of the dsODN are phosphorylated.

A4. The foregoing method of A-A3, wherein the dsODN comprises phosphorothioate linkages on both 3' ends.

A5. The foregoing method of A-A4, wherein the dsODN comprises phosphorothioate linkages on both 3' ends and both 5' ends.

A6. The foregoing method of A-A7, wherein the dsODN is between about 15 and about 50 nucleotides long.

A7. The foregoing method of A-A6, wherein amplifying a portion of the genomic DNA comprises fragmenting the genomic DNA; ligating ends of the fragmented genomic DNA with a universal adapter; performing a first round of polymerase chain reaction (PCR) on the ligated DNA with a first primer that is complementary to the integrated dsODN and a second primer that is complementary to the universal adapter; and performing a second round of PCR using a third primer that is a 3' nested primer and is complementary to the first primer, a fourth primer that is a 3' nested primer and is complementary to the second primer, and a fifth primer that is complementary to the fourth primer.

A8. The foregoing method of A7, wherein the fifth primer a purification sequence, a binding sequence, an identification sequence, or a combination thereof.

A9. The foregoing method of A-A8, wherein the nuclease composition comprises a meganuclease, a zinc-finger nuclease, a TALEN nuclease, a Cas nuclease.

A10. The foregoing method of A-A9, wherein the nuclease composition comprises a ribonucleoprotein (RNP) complex.

A11. The foregoing method of A10, wherein the RNP complex comprises a Cas9 nuclease and a guide RNA.

A12. The foregoing method of A11, wherein the Cas9: guide RNA molar ratio is from about 1:4 to about 1:7.

A13. The foregoing method of A12, wherein the Cas9: guide RNA molar ratio is about 1:6.

A14. The foregoing method of A10-A13, wherein the Cas9 nuclease is at an amount ranging from about 15 µg to about 30 µg per RNP complex.

A15. The foregoing method of A14, wherein the Cas9 nuclease is at an amount of about 16 µg per RNP complex.

A16. The foregoing method of A11-A15, wherein the gRNA is at an amount ranging from about 500 pmol to about 750 pmol per RNP complex.

A17. The foregoing method of A16, wherein the gRNA is at an amount of about 600 pmol per RNP complex.

A18. The foregoing method of A-A17, wherein the nuclease composition targets a TRAC locus.

A19. The foregoing method of A-A18, wherein the nuclease composition targets a TRBC locus.

A20. The foregoing method of A-A19, wherein the guide RNA targets a TRAC locus and/or a TRBC locus.

A21. The foregoing method of A-A20, wherein the DSB is an off-target DSB.

A22. The foregoing method of A-A21, wherein the dsODN comprises a DNA barcode.

A23. The foregoing method of A22, wherein the DNA barcode is randomized.

A24. The foregoing method of A-A23, wherein the dsODN comprises a nucleotide sequence set forth in SEQ ID NO: 1 and SEQ ID NO: 2.

A25. The foregoing method of A-A24, wherein the nuclease composition is delivered by a non-viral delivery system.

A26. The foregoing method of A25, wherein the nuclease composition is delivered by electroporation.

A27. The foregoing method of A-A26, wherein the nucleotide composition is delivered by a non-viral delivery system.

A28. The foregoing method of A27, wherein the nucleotide composition is delivered by electroporation.

A29. The foregoing method of A-A28, wherein the primary cell is a mammalian cell.

A30. The foregoing method of A-A29, wherein the primary cell is a human cell.

A31. The foregoing method of A30, wherein the human cell is a hematopoietic stem cell.

A32. The foregoing method of A31, wherein the human cell is a T cell.

A33. The foregoing method of A32, wherein the T cell is a cytotoxic T cell, a memory T cell, a regulatory T cell, a tumor-infiltrating T cell, a natural killer T cell.

A34. The foregoing method of A32 or A33, wherein the T cell is a CD8+ T cell or a CD4+T cell.

A35. The foregoing method of A30, wherein the human cell is an NK cell.

A36. The foregoing method of A-A35, wherein the primary cell is obtained from a subject.

A37. The foregoing method of A36, wherein the subject is human.

EXAMPLES

The following are examples of methods and compositions of the present disclosure. It is understood that various other embodiments may be practiced, given the general description provided above.

Example 1. Primary T-Cell GUIDE-Seq.

Primary T-cell GUIDE-Seq was performed on isolated CD4 and CD8 T-cells using the TRAC and TRBC guide RNAs according to published protocols (see, e.g., Tsai et al., 2015 and PCT Publication WO 2015/200378, "Genomewide Unbiased Identification of DSBS Evaluated by Sequencing (GUIDE-Seq), incorporated by reference in its entirety) with culturing and nucleofection conditions modified for primary T-cells, as described below.

Cell Culture and Nucleofection

CD4 and CD8 enriched T-cells, originally obtained from a healthy donor leukopak, were isolated on the Miltenyi Prodigy or Miltenyi MACS separation columns according to the manufacturers' instructions.

Double-stranded oligonucleotides (dsODN) used to mark double-stranded break (DSB) sites were purchased as custom-synthesized and annealed strands. The following dsODN sequences were used, where P represents 5' phosphorylation, and * indicates a phosphorothioate linkage:

```
                                        (SEQ ID NO: 1)
5' P-G*T*TTAATTGAGTTGTCATATGTTAATAACGGT*A*T 3'

(SEQ ID NO: 2)
3' C*A*AATTAACTCAACAGTATACAATTATTGCCA*T*A-P 5'
```

Electroporation was performed on a Lonza 4-D Nucleofector X-unit in 100 μL cuvettes. Each electroporation used 5E6 T-cells, 10 μg of dsODN, and Cas9 ribonucleoprotein complexes (RNPs) complexed at 1:6 Cas9:sgRNA molar ratio. Cells were then grown in culture medium with 100 U/ml of penicillin and 100 μg/ml of streptomycin. Cells were harvested 72 hours after nucleofection, and genomic DNA (gDNA) was isolated using the Nucleospin Tissue Kit (Macherey-Nagel) following the manufacturer's standard protocol. Isolated genomic DNA was quantitated using a Nanodrop spectrophotometer.

Restriction Fragment Length Polymorphism (RFLP) Confirmation of doODN Integration TRAC (T Cell Receptor Alpha Constant), TRBC1 (T Cell Receptor Beta Constant 1), and TRBC2 (T Cell Receptor Alpha Constant 2) sites in the isolated genomic DNA were amplified using PCR with the primers in the table below:

TABLE 1

PCR Primers Used for RFLPCR Primers for RFLP

| Target | Primer | Sequence | Amplicon (bp) |
|---|---|---|---|
| TRAC | TRAC F | TCACGAGCAGCTGGTTTCTA (SEQ ID NO: 3) | 580 |
|  | TRAC R | GGGTTTTGGTGGCAATGGAT (SEQ ID NO: 4) |  |
| TRBC1 | TRBC1 F | CAACAGACACTGGGATGGTG (SEQ ID NO: 5) | 731 |
|  | TRBC1 R | GCTCTGTTGGGCTGAGAATC (SEQ ID NO: 6) |  |
| TRBC2 | TRBC2 F | CTAACGGGGGATGGACAGA (SEQ ID NO: 7) | 842 |
|  | TRBC2 R | GAGCTTGAGGTGCTCCATTC (SEQ ID NO: 8) |  |

Each site was amplified using 100 ng gDNA with KOD Hot Start Master Mix (Millipore Sigma) with the following thermal cycling conditions: 95° C. for 120 s, 7 cycles (95° C. for 20 s, 68° C. for 10 s (−1 ° C./cycle); 70° C. for 15 s), 26 cycles (95° C. for 20 s, 60° C. for 10 s, 70° C. for 15 s) 70° C. for 5 min, 4° C., until sample was removed.

Figure 1:
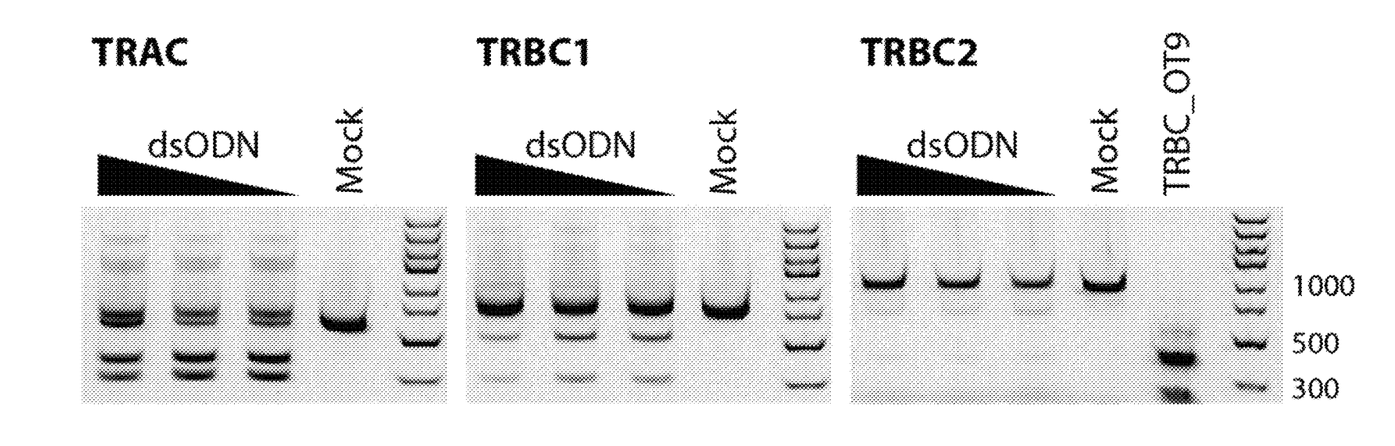
FIG. 1 illustrates dsODN integration efficiency via electroporation of human T cells with Cas9 RNPs targeting TRAC, TRBC1, and TRBC2 as measured by running TRAC, TRBC1, and TRBC2 amplicons from electroporated T cells that were digested with NdeI restriction enzyme on a 2% agarose gel. dsODN amount was varied at 5, 10, and 20 μg per reaction with TRAC, TRBC1, and TRBC2 Cas9 RNPs. dsODN amount corresponds with the wedge height shown on each gel image under 'dsODN.'

Amplicon sizes were confirmed on a 2% agarose gel and the correct size amplicons purified using the ZR-96 DNA Clean-up Kit (Zymo Research). 200 ng of each amplicon was digested with 5 U NdeI restriction enzyme (New England Biolabs) in a 20 μl reaction at 37° C. for >2 hours, and digested products were analyzed on a 2% agarose gel (see, e.g., FIG. 1). Amplicons made using mock electroporated T cell DNA were used as a negative control. Amplicons, which naturally contains a NdeI restriction site, were used as a positive control for NdeI cutting.

DNA Processing and Sequencing

Three aliquots (900 ng per aliquot) of each DNA sample were sheared with a Covaris M220 and a portion analyzed on a gel. Aliquots of each sample with mean fragment sizes close to 500 bp were pooled, end-repaired, A-tailed, and Y-adapter-ligated. The first round of dsODN integration site PCR was performed for sense and antisense strands using primers specific to the dsODN tag used during transfection (+ and − strand GSP1) and a P5 primer. A second round of dsODN integration site PCR was performed with nested primers for the dsODN (+ and − strand GSP2) and P5 primer.

Samples were purified and concentrated using 1× beads (GE, Sera-Mag Select). Quantification of final libraries was performed using the Qubit High Sensitivity dsDNA assay (Thermo Fisher). Libraries for both replicates of TRAC+tag sense/antisense and TRBC+tag sense/antisense were mixed in equal molar concentrations and loaded into a 500 cycle version 2 Illumina kit and run on a MiSeq (Illumina). TRAC and TRBC samples were sequenced in separate MiSeq runs.

Data Analysis

MiSeq reads were analyzed using the published script (https://github.com/aryeelab/guideseq). This script takes reads from a FASTQ file and uses the unique molecular identifiers (UMIs) in the P5 primers to remove PCR duplicates. It then aligns reads to the genome and uses read pile-ups to call potential off-target sites. Potential sites are further filtered using a penalty function to remove false positives, and sites that remain after filtering are output along with genomic annotations. The script was run using standard options, except that the penalty for mismatches was set to 10 instead of the usual 100, since CRISPR off-target cutting has been observed in sites that have mismatches relative to the guide strand sequence (Lin et al 2014).

Results

The concentration of dsODN used in the electroporation mix was optimized as follows: First T cells were electroporated using three doses of dsODN: 5, 10, and 20 μg per reaction. Electroporations for TRAC and TRBC Cas9 RNPs were performed separately. TRAC, TRBC1, and TRBC2 sites were amplified as described above under "RFLP confirmation of dsODN integration." Amplicons were digested using 5 U NdeI restriction enzyme and digested products were analyzed on a 2% agarose gel. Mock electroporated T cell DNA was used as a negative control. A positive control that contains a NdeI restriction site was used as well. FIG. 1 and Table 2 show results for this initial optimization.

TABLE 2

Cas9 RNP Cutting Efficiencies, Determined
from Measuring Bands Shown in FIG. 1

| dsODN Dose | TRAC cutting efficiency | TRBC1 cutting efficiency | TRBC2 cutting efficiency | Avg cutting efficiency |
|---|---|---|---|---|
| 20 μg | 46.40% | 18.00% | 2.60% | 22.30% |
| 10 μg | 59.70% | 32.30% | 5.00% | 32.30% |
| 5 μg | 57.80% | 29.70% | 14.60% | 34.00% |

As shown in Table 2 and FIG. 1, cutting efficiencies decreased dramatically when higher amount of dsODNs were used (see decrease from 10 μg dsODN to 20 μg dsODN), with very little difference in average cutting efficiency between 10 μg of dsODN and 5 μg of dsODN. Therefore, to capture most of the dsODN integration signal, all later experiments used dsODN at the single dose of 10 μg per electroporation.

To identify potentially cell-type relevant CRISPR off-target sites, GUIDE-Seq was performed using primary human T cells electroporated with Cas9 RNPs made with the sgRNAs used for engineered T cell manufacturing. T cells from two human donor samples were electroporated with both Cas9 RNP complexed with a TRAC sgRNA and Cas9 RNP complexed with a TRBC sgRNA at the same time. Electroporation and analysis were performed for replicate electroporation runs in both studies; the use of biological replicates allowed further assessment of measurement sensitivity and noise. As expected, sites with the most frequent GUIDE-Seq read counts were the on-target TRAC and TRBC sites (See, e.g., Table 3). Integration of the dsODN tag at each on-target locus was also confirmed orthogonally by restriction fragment length polymorphism analysis (RFLP). Therefore, the primary T cell GUIDE-Seq procedure successfully integrates dsODNs at sites of double-stranded cleavage sites within the T-cell genome. Similar to results from GUIDE-Seq using U2OS cells, primary T-cell GUIDE-Seq did not identify any off-target sites originating from the TRAC guide RNA (Table 3).

TABLE 3

On-Target Sites Originating from the TRAC Guide RNA

| | Reads (run #1) | Reads (run #2) | dsODN integration site sequence | Closest | Site gene | type |
|---|---|---|---|---|---|---|
| target sequence | | | | GAGAATCAAAATCGGTGAATNGG (SEQ ID NO: 9) | | |
| Donor Sample 1 | 18009 | 28574 | 1 | GAGAATCAAAATCGGTGAATAGG (SEQ ID NO: 10) | TCRA | On target |
| Donor Sample 2 | 17726 | 5707 | 1 | GAGAATCAAAATCGGTGAATAGG (SEQ ID NO: 11) | TCRA | On target |

Example 2. Primary T-Cell GUIDE-Seq Cell Culture and Transfection

Primary T-cell GUIDE-Seq was performed on isolated CD4 and CD8 T-cells using the method entitled "New PACT Process," provided in Table 4.

TABLE 4

The New PACT Process and Differences in Between Such and The Original

| | Original process (U2OS) | Original process (HEK293) | New PACT process (Primary Human Cells) |
|---|---|---|---|
| Cell Type | U2OS | HEK293 | Primary cells |
| Media type, serum, antibiotics | Advanced DMEM, 10% FBS, pen/strep | | TexMACS, 3% human serum, pen/strep |
| Cas9 | Plasmid expression (500 ng of pCAG-Cas9) | Plasmid expression (300 ng of pCAG-Cas9) | Ribonucleotide delivery (16.7 ug Cas9 per RNP) |
| Guide RNA (approximate) | Plasmid expression (250 ng) | Plasmid expression (150 ng) | Ribonucleotide delivery (600 pmol sgRNA per RNP) |
| dsODN (approximate molar concentration) | 100 pmol dsODN | 5 pmol dsODN | 472 pmol dsODN |

As shown in Table 4, there are significant differences in the dsODN and Guide RNA used for known Guide-Seq methods used on non-primary cell lines compared to the new transfection conditions used for primary cells. Furthermore, the expression of Cas9 was accomplished in primary cells using ribonucleoprotein (RNP) whereas plasmid expression was sufficient in non-primary cell lines. These differences proved key to discovering how to use the Guide-Seq method on primary cells.

While specific media was used for exemplary purposes in the experiment provided in Table 4, any media for the cultivation of primary cells could be used based on what is known by one of skill in the art.

Furthermore, as shown in Table 5, Nucleofection was used to transfect primary cells and, as described above, there were significant differences in the dsODN and Guide RNA used for known Guide-Seq methods used on non-primary cell lines compared to the new transfection conditions used for primary cells when nucleofection was used.

TABLE 5

Transfection Conditions for the new PACT Process used on Primary T Cells

| | Original process (U2OS) | Original process (HEK293) | New PACT process (Primary Human Cells) |
|---|---|---|---|
| Cell Type | U2OS | HEK293 | Primary T cells |
| Media type, serum, antibiotics | Advanced DMEM, 10% FBS, pen/strep | Advanced DMEM, 10% FBS, pen/strep | TexMACS, 3% human serum, pen/strep |
| Nucleofection Program | DN-100 | CM-137 | EO-115 |
| Nucleofection Buffer | Solution SE | Solution SE | P3 Primary Cell Solution |
| Cas9 | Plasmid expression (500 ng of pCAG-Cas9) | Plasmid expression (300 ng of pCAG-Cas9) | Ribonucleotide delivery (16.7 ug Cas9 per RNP) |
| Guide RNA (approximate) | Plasmid expression (250 ng) | Plasmid expression (150 ng) | Ribonucleotide delivery (600 pmol sgRNA per RNP) |
| Nucleofection Scale | 20 uL | 20 uL | 100 uL |
| dsODN (approximate molar concentration) | 100 pmol dsODN | 5 pmol dsODN | 472 pmol dsODN |

While specific media was used for exemplary purposes in the experiment provided in Table 5, any media for the cultivation of primary T cells could be used based on what is known by one of skill in the art.

Accordingly, it has been shown that the PACT process for transfecting cells for Guide-Seq is successful for primary T cells.

REFERENCES

Cradick, T. J. et al. (2014) 'COSMID: A Web-based Tool for Identifying and Validating CRISPR/Cas Off-target Sites.', Molecular Therapy—Nucleic acids. American Society of Gene & Cell Therapy, 3(12), p. e214. doi: 10.1038/mtna.2014.64.

Kim, D. and Kim, J.-S. (2018) 'DIG-seq: a genome-wide CRISPR off-target profiling method using chromatin DNA.', Genome research. Cold Spring Harbor Laboratory Press, 28(12), pp. 1894-1900. doi: 10.1101/gr.236620.118.

Lin, Y. et al. (2014) 'CRISPR/Cas9 systems have off-target activity with insertions or deletions between target DNA and guide RNA sequences', Nucleic Acids Research. Oxford University Press, 42(11), p. 7473. doi: 10.1093/NAR/GKU402.

Tsai, S. Q. et al. (2015) 'GUIDE-Seq enables genome-wide profiling of off-target cleavage by CRISPR-Cas nucleases', Nature Biotechnology. Nature Publishing Group, a division of Macmillan Publishers Limited. All Rights Reserved., 33(2), pp. 187-197. doi: 10.1038/nbt.3117.

OTHER EMBODIMENTS

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes. In case of conflict, the present specification, including definitions, will control. In addition, section headings, the materials, methods, and examples are illustrative only and not intended to be limiting.

What is claimed is:

1. A method for detecting double-stranded breaks (DSBs) in genomic DNA of a primary human T cell, the method comprising:
   a. providing a nuclease composition comprising a ribonucleotide (RNP) complex comprising a Cas9 nuclease and a guide RNA (gRNA), wherein the RNP complex is capable of inducing a double-stranded break in the genomic DNA of a primary cell, wherein the amount of the gRNA is from 600 pmol to 750 pmol per RNP complex;
   b. providing a nucleotide composition comprising a blunt-ended double stranded oligonucleotide (dsODN), wherein the amount of dsODN is 5 µg to 10 µg;
   c. incubating the primary cell with the RNP complex for a time sufficient for inducing DSBs in the genomic DNA of the cell, repairing the DSBs, and integrating the dsODN at one or more DSBs;
   d. amplifying a portion of the genomic DNA comprising the integrated dsODN; and
   e. sequencing the amplified portion of the genomic DNA, thereby detecting a DSB in the genomic DNA of the primary cell.

2. The method of claim 1, wherein both strands of the dsODN are orthogonal to the genome of the cell.

3. The method of claim 1, wherein the 5' ends of the dsODN are phosphorylated.

4. The method of claim 1, wherein the dsODN comprises phosphorothioate linkages on both 3' ends.

5. The method of claim 1, wherein the dsODN comprises phosphorothioate linkages on both 3' ends and both 5' ends.

6. The method of claim 1, wherein the dsODN is between 15 and 50 nucleotides long.

7. The method of claim 1, wherein amplifying a portion of the genomic DNA comprises:
   a. fragmenting the genomic DNA;
   b. ligating ends of the fragmented genomic DNA with a universal adapter;
   c. performing a first round of polymerase chain reaction (PCR) on the ligated DNA with a first primer that is complementary to the integrated dsODN and a second primer that is complementary to the universal adapter; and
   d. performing a second round of PCR using a third primer that is a 3' nested primer and is complementary to the first primer, a fourth primer that is a 3' nested primer and is complementary to the second primer, and a fifth primer that is complementary to the fourth primer.

8. The method of claim 7, wherein the fifth primer comprises a purification sequence, a binding sequence, an identification sequence, or a combination thereof.

9. The method of claim 1, wherein the Cas9: guide RNA molar ratio is from 1:4 to 1:7.

10. The method of claim 1, wherein the amount of the Cas9 nuclease is from 15 µg to 30 µg per RNP complex.

11. The method of claim 1, wherein the guide RNA targets a TRAC locus and/or a TRBC locus.

12. The method of claim 1, wherein the DSB is an off-target DSB.

13. The method of claim 1, wherein the dsODN comprises a DNA barcode.

14. The method of claim 1, wherein the nuclease composition is delivered by a non-viral delivery system.

15. The method of claim 1, wherein the nucleotide composition is delivered by a non- viral delivery system.

16. The method of claim 1, wherein the T cell is a cytotoxic T cell, a memory T cell, a regulatory T cell, a tumor-infiltrating T cell, or a natural killer T cell.

17. The method of claim 1, wherein the T cell is a CD8+ T cell or a CD4+ T cell.

* * * * *